(12) United States Patent
Qi et al.

(10) Patent No.: US 8,329,895 B2
(45) Date of Patent: Dec. 11, 2012

(54) CEFDINIR ACID DOUBLE SALT AND METHOD FOR PRODUCING THE SAME

(75) Inventors: Youmao Qi, Hangzhou (CN); Fengqi Ye, Hangzhou (CN); Qing Jie, Hangzhou (CN); Yingbei Qi, Hangzhou (CN); Fengmin Zhang, Hangzhou (CN); Baochun Yu, Hangzhou (CN); Tianjian Ye, Hangzhou (CN); Meiping Yu, Hangzhou (CN)

(73) Assignees: Zhejiang Adamerck Biopharmlabs Inc., Hangzhou (CN); Zhejiang Yongning Pharma Co., Ltd., Taizhou (CN)

( * ) Notice: Subject to any disclaimer, the term of this patent is extended or adjusted under 35 U.S.C. 154(b) by 0 days.

(21) Appl. No.: 13/172,907

(22) Filed: Jun. 30, 2011

(65) Prior Publication Data

US 2011/0257388 A1 Oct. 20, 2011

Related U.S. Application Data

(63) Continuation of application No. PCT/CN2009/076164, filed on Dec. 29, 2009.

(30) Foreign Application Priority Data

Dec. 31, 2008 (CN) .......................... 2008 1 0164211

(51) Int. Cl.
*C07D 501/22* (2006.01)
(52) U.S. Cl. ...................................... 540/222
(58) Field of Classification Search ............... None
See application file for complete search history.

(56) References Cited

U.S. PATENT DOCUMENTS

| | | | | |
|---|---|---|---|---|
| 4,559,334 A * | 12/1985 | Takaya et al. | ................. | 514/202 |
| 6,093,814 A * | 7/2000 | Lee et al. | ..................... | 540/222 |
| 6,350,869 B1 * | 2/2002 | Sturm et al. | .................. | 540/220 |
| 7,157,576 B2 * | 1/2007 | Lee et al. | ..................... | 540/222 |
| 7,173,126 B2 * | 2/2007 | Pozzi et al. | .................... | 540/222 |
| 7,405,294 B2 * | 7/2008 | Pozzi et al. | .................... | 540/222 |
| 2007/0191602 A1 * | 8/2007 | Kansal et al. | ................. | 540/222 |
| 2008/0033169 A1 * | 2/2008 | Pozzi et al. | ..................... | 544/54 |
| 2009/0036672 A1 * | 2/2009 | Pozzi et al. | .................... | 540/222 |

FOREIGN PATENT DOCUMENTS

| CN | 101481383 A | * | 7/2009 |
|---|---|---|---|
| WO | WO 2010075765 A1 | * | 7/2010 |

OTHER PUBLICATIONS

CN101481383A Translation (Jul. 2009).*

* cited by examiner

*Primary Examiner* — Mark Berch
(74) *Attorney, Agent, or Firm* — Matthias Scholl P.C.; Matthias Scholl

(57) ABSTRACT

A compound represented by Formula I,

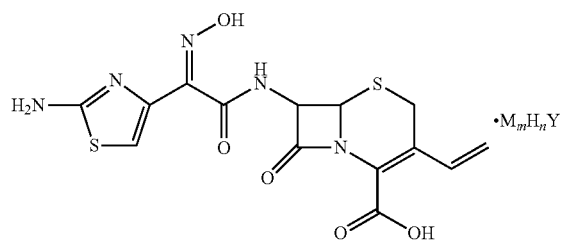

Formula I wherein M represents $Na^+$, $K^+$, $NH_4^+$, or $Cs^+$; and 1) when Y represents $SO_4^{2-}$: when m=1, then n=1; and when m=0.5, then n=1.5; and 2) when Y represents $PO_4^{3-}$, when m=1, then n=2. The compound has good solubility and high bioavailability and can be formulated into oral pharmaceutical preparations and pharmaceutical preparations for injections.

10 Claims, No Drawings

CEFDINIR ACID DOUBLE SALT AND METHOD FOR PRODUCING THE SAME

CROSS-REFERENCE TO RELATED APPLICATIONS

This application is a continuation of International Patent Application No. PCT/CN2009/076164 with an international filing date of Dec. 29, 2009, designating the United States, now pending, and further claims priority benefits to Chinese Patent Application No. 200810164211.3 filed Dec. 31, 2008. The contents of all of the aforementioned applications, including any intervening amendments thereto, are incorporated herein by reference.

BACKGROUND OF THE INVENTION

1. Field of the Invention

The invention relates to a compound and method for producing the same, and more particularly to a cefdinir acid double salt, a preparation method, and use thereof.

2. Description of the Related Art

Cefdinir was first synthesized by Fujisawa Company, Japan, in 1988 by modifying the structure of cefixime. It is the third generation of oral cephalosporin. The vinyl group linked to a mother ring carbon of cephalosporin improves the oral absorption rate thereof. The hydroxyl amino group and ammonia thiophene group at the side chain not only enhance the antibacterial activity against gram-negative bacteria and the stability of β-lactamase, but also improve the antibacterial activity against gram-positive bacteria, particularly against *Staphylococcus aureus*. The cefdinir preparations were first approved for sale in Japan in December, 1991, with a brand name of Cefzon, and then were sold in USA in December, 1997, with a brand name of Omnicef, and in Korea in 1999. Tianjin Centralpharm Co., Ltd. and Tianjin Institute of Pharmaceutical Research have cooperatively developed the production and synthesis of cefdinir and the dosage form of capsules and granules are obtained. The capsules have a brand name of Cefdinir Capsules, approved for sale in 2001 in China.

With a broad antimicrobial spectrum, high activity, good drug resistance, cefdinir is very excellent in the third generation of cephalosporin. However, it has obvious disadvantages such as low solubility and low bioavailability. Study shows that capsule cefdinir has a bioavailability of 16-20%, and for a liquid suspension, the bioavailability is merely 25%. Low bioavailability wastes drug resources, and the antibiotic residues easily cause side effect, e.g., intestinal flora disturbance and diarrhea. Furthermore, cefdinir is insoluble in water, and thus it cannot be prepared into an injection directly.

To solve the above disadvantages, a large number of researches have been conducted. Since the chemical structure of cefdinir includes carboxylic acids and amino group, a basic salt or acid salt thereof has been disclosed.

Chinese Pat. CN 1,415,615 discloses sodium cefdinir and a preparation method thereof. Chinese Pat. CN 1,251,590 discloses a salt synthesized by cefdinir and dicyclohexylamine. Chinese Pat. CN 1,512,996 discloses sulfate or mesylate cefdinir. U.S. Pat. No. 4,559,334 discloses the following cefdinir salt: sodium, potassium, calcium, magnesium, ammonium, organic ammonium, hydrochloric acid, sulfuric acid, bromated, phosphoric acid, formic acid, acetic acid, trifluoroacetic acid, maleic acid, tartaric acid, methanesulfonic acid, benzoic acid, arginine, aspartic acid, glutamic acid. KR20070088757 discloses a method for producing cesium cefdinir to purify cefdinir. DE60311869 discloses a method for producing phosphate cefdinir to purify cefdinir.

Cefdinir basic salts have poor stability.

The cefdinir salts recited in the above patents mainly target the purification of cefdinir. Prior to this disclosure, no cefdinir acid double salts or the benefits thereof have been reported.

SUMMARY OF THE INVENTION

In view of the above-described problems, it is one objective of the invention to provide a cefdinir acid double salt.

It is another objective of the invention to provide a method for producing a cefdinir acid double salt.

To achieve the above objectives, in accordance with one embodiment of the invention, there is provided a cefdinir acid double salt represented by Formula I:

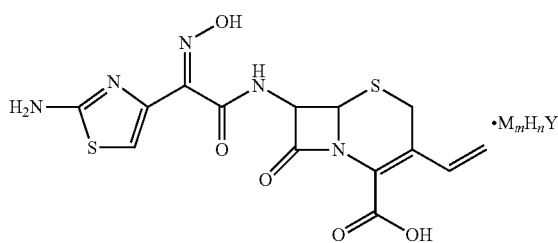

Formula I wherein M represents $Na^+$, $K^+$, $NH_4^+$, or $Cs^+$; and 1) when Y represents $SO_4^{2-}$ and m=1, n=1; when m=0.5, n=1.5; 2) when Y represents $PO_4^{3-}$=1, n=2.

In accordance with another embodiment of the invention, there is provided a method for producing the cefdinir acid double salt. The method comprises contacting cefdinir with an acid and an alkali or ammonium compound, or contacting cefdinir with an acid salt. When the acid or acid salt comprises a sulfate group, the product is a cefdinir hydrogen sulfate double salt. When the acid or acid salt comprises a phosphate group, the product is a cefdinir dihydrogen phosphate double salt.

In a class of this embodiment, the cefdinir hydrogen sulfate double salt is prepared as follows. 1) Cefdinir and equimolar sulfuric acid is mixed, and then an alkali compound with a molar ratio to cefdinir of 0.5:1 or 1:1 is added. The resultant product is concentrated, crystallized with ether, filtered, and dried to yield cefdinir sodium(1 or 0.5) hydrogen(1 or 1.5) sulfate, cefdinir potassium(1 or 0.5) hydrogen(1 or 1.5) sulfate, or cefdinir cesium(1 or 0.5) hydrogen(1 or 1.5) sulfate. 2) Cefdinir and equimolar sulfuric acid is mixed, and then ammonium acetate, ammonia gas, or ammonia water with a molar ratio to cefdinir of 0.5:1 or 1:1 is added. The resultant product is concentrated, crystallized with ether, filtered, and dried to yield cefdinir ammonium (1 or 0.5) hydrogen (1 or 1.5) sulfate. 3) Cefdinir and equimolar sodium hydrogen sulfate, potassium hydrogen sulfate, or ammonium hydrogen sulfate is mixed. The resultant product is concentrated, crystallized with ether, filtered, and dried to yield a cefdinir hydrogen sulfate double salt.

In a class of this embodiment, the cefdinir hydrogen sulfate double salt is represented by the following formulas:

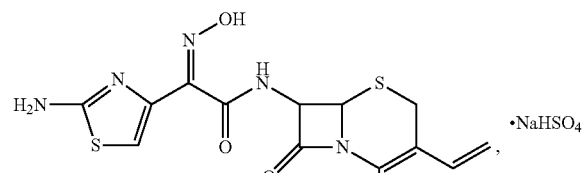
·NaHSO$_4$,

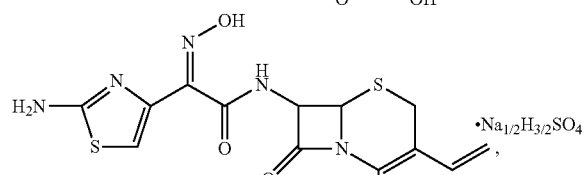
·Na$_{1/2}$H$_{3/2}$SO$_4$,

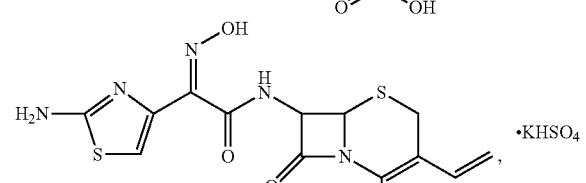
·KHSO$_4$,

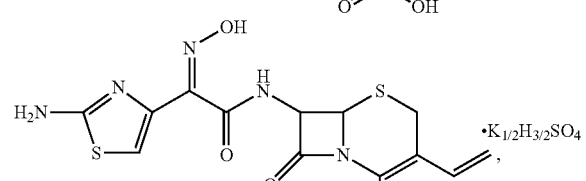
·K$_{1/2}$H$_{3/2}$SO$_4$,

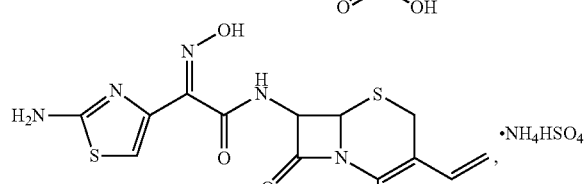
·NH$_4$HSO$_4$,

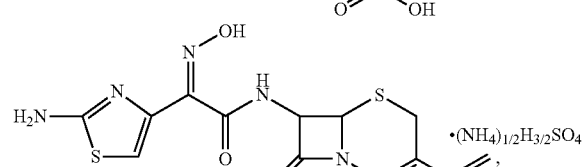
·(NH$_4$)$_{1/2}$H$_{3/2}$SO$_4$,

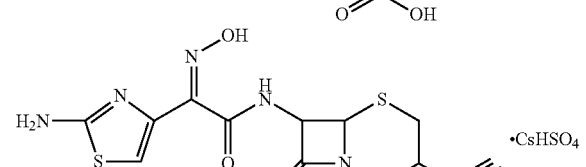
·CsHSO$_4$,

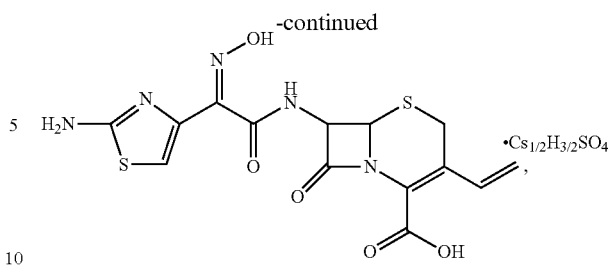
·Cs$_{1/2}$H$_{3/2}$SO$_4$,

In a class of this embodiment, the cefdinir dihydrogen phosphate double salt is prepared as follows. 1) Cefdinir and equimolar phosphoric acid is mixed, and then an alkali compound with a molar ratio to cefdinir of 1:1 is added. The resultant product is concentrated, crystallized with ether, filtered, and dried to yield cefdinir sodium dihydrogen phosphate, cefdinir potassium dihydrogen phosphate, or cefdinir cesium dihydrogen phosphate. 2) Cefdinir and equimolar phosphoric acid is mixed, and then ammonium acetate, ammonia gas, or ammonia water with a molar ratio to cefdinir of 1:1 is added. The resultant product is concentrated, crystallized with ether, filtered, and dried to yield cefdinir ammonium dihydrogen phosphate. 3) Cefdinir and equimolar sodium dihydrogen phosphate, potassium dihydrogen phosphate, or ammonium dihydrogen phosphate is mixed. The resultant product is concentrated, crystallized with ether, filtered, and dried to yield cefdinir sodium dihydrogen phosphate, cefdinir potassium dihydrogen phosphate, or cefdinir ammonium dihydrogen phosphate.

In a class of this embodiment, the cefdinir dihydrogen phosphate double salt is represented by the following formulas:

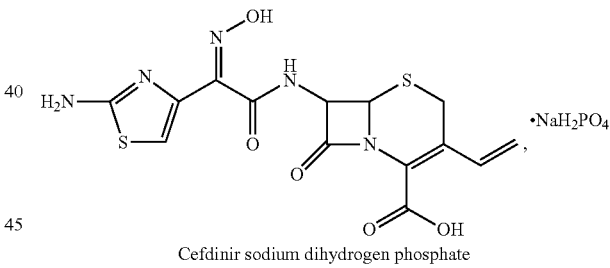
·NaH$_2$PO$_4$
Cefdinir sodium dihydrogen phosphate

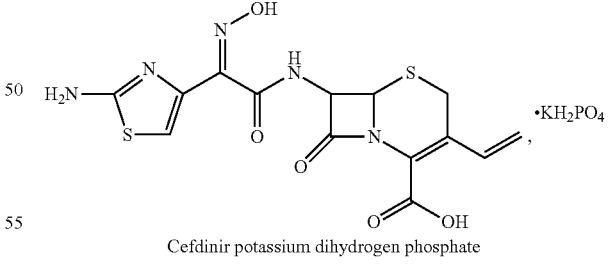
·KH$_2$PO$_4$
Cefdinir potassium dihydrogen phosphate

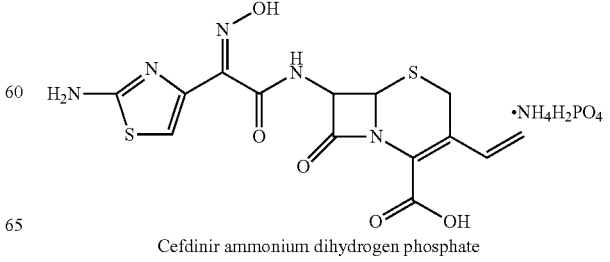
·NH$_4$H$_2$PO$_4$
Cefdinir ammonium dihydrogen phosphate

-continued

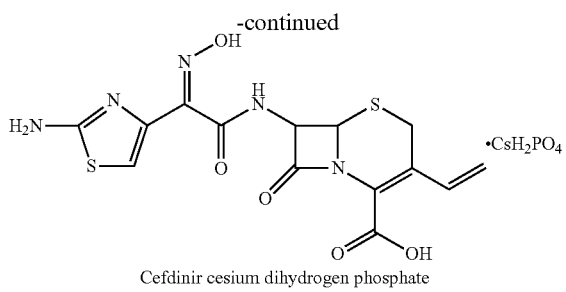

Cefdinir cesium dihydrogen phosphate

In a class of this embodiment, the alkali compound is selected from the group consisting of sodium methoxide, potassium methoxide, cesium methoxide, sodium ethoxide, potassium ethoxide, cesium ethoxide, sodium propoxide, potassium propoxide, cesium propoxide, sodium butoxide, potassium butoxide, cesium butoxide, sodium isopropoxide, potassium isopropoxide, cesium isopropoxide, sodium tert-butoxide, potassium tert-butoxide, cesium tert-butoxide, sodium acetate, potassium acetate, cesium acetate, sodium propionate, potassium propionate, cesium propionate, sodium butyrate, potassium butyrate, cesium butyrate, sodium hydroxide, potassium hydroxide, and cesium hydroxide.

In a class of this embodiment, the ammonium compound is selected from the group consisting of ammonia, ammonia water, ammonium acetate, ammonium propionate, and ammonium butyrate.

In a class of this embodiment, the cefdinir hydrogen sulfate double salt comprises (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid sodium hydrogen sulfate, (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid potassium hydrogen sulfate, (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid ammonium hydrogen sulfate, and (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid cesium hydrogen sulfate. The cefdinir hydrogen sulfate double salt further comprises (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid sodium(0.5) hydrogen(1.5) sulfate, (−)-(6R, 7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid potassium(0.5) hydrogen(1.5) sulfate, (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid ammonium(0.5) hydrogen(1.5) sulfate, and (−)-(6R, 7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid cesium(0.5) hydrogen(1.5) sulfate.

In a class of this embodiment, the cefdinir dihydrogen phosphate double salt comprises (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid sodium dihydrogen phosphate, (−)-(6R,7R)-7-((Z)-2-(2-aminothiazole-4-yl)-2-hydroxyimino-acetylamino) 8-oxo-3-vinyl-5-thia-1-azabicyclo(4.2.0)oct-2-ene-2-carboxylic acid potassium dihydrogen phosphate, and (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid ammonium dihydrogen phosphate, and (−)-(6R,7R)-7-((Z)-2-(2-aminothiazole-4-yl)-2-hydroxyimino-acetylamino)-8-oxo-3-vinyl-5-thia-1-azabicyclo(4.2.0)oct-2-ene-2-carboxylic acid cesium dihydrogen phosphate.)

Advantages of the invention are summarized below.

The cefdinir hydrogen sulfate double salt and cefdinir dihydrogen phosphate double salt have good stability, good solubility, and thus the bioavailability thereof have been enhanced greatly. The double salts can be administered orally or by injection.)

The melting point of the double salts is still under study. Above 203° C., the double salts turn yellow, above 270° C., turn brown, and at 303° C., the salts don't disappear. The sodium cefdinir disclosed in CN 1,415,615A turns yellow at about 160° C., and turns black at 190° C. and finally disappear. Obviously, in contrast to the prior art, the double salts of the invention have better stability.

Cefdinir has a broad antimicrobial spectrum and good antibacterial activity against gram-positive and -negative bacteria, e.g., *Moraxella catarrhalis, Klebsiella pneumoniae*, proteobacteria, and *Escherichia coli*. Furthermore, cefdinir is stable to β-lactamase and can kill some bacteria capable of synthesizing enzyme. With good water solubility, the double salts can be prepared into solid formulations or injections.

The method for producing the double salts has a stable process and high manufacturing feasibility. The compound (double salts) has good solubility and high bioavailability, and exhibits high activity and high efficiency in clinical practice.

DETAILED DESCRIPTION OF THE EMBODIMENTS

For further illustrating the invention, experiments detailing a cefdinir double salt and preparation method thereof are described below. It should be noted that the following examples are intended to describe and not to limit the invention.

Example 1

To a 100 mL reaction flask, 2.0 g of cefdinir and 20 mL of anhydrous methanol were added and stirred to yield a uniform mixture. 0.496 g of sulfuric acid was diluted with 10 mL of anhydrous methanol, and the resulting solution was dripped slowly into the uniform mixture under an ice bath condition. After the solution was clear, 0.273 g of sodium methoxide was added and allowed to react for 15 min. Subsequently, methanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 99%, with a content of 98.7% and purity greater than or equal to 99%.

Example 2

To a 100 mL reaction flask, 2.0 g of cefdinir and 20 mL of anhydrous ethanol were added and stirred to yield a uniform mixture. 0.496 g of sulfuric acid was diluted with 10 mL of anhydrous ethanol, and the resulting solution was dripped slowly into the uniform mixture under an ice bath condition. After the solution was clear, 0.1365 g of sodium methoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium(0.5) hydrogen(1.5) sulfate obtained. The yield was 98.1%, with a content of 98.4% and purity greater than or equal to 99%.

Example 3

To a 100 mL reaction flask, 2.0 g of cefdinir and 20 mL of anhydrous methanol were added and stirred to yield a uniform mixture. 0.496 g of sulfuric acid was diluted with 10 mL of anhydrous methanol, and the resulting solution was dripped slowly into the uniform mixture under an ice bath condition. After the solution was clear, 0.355 g of potassium methoxide was added and allowed to react for 15 min. Subsequently, methanol was distilled off at 40° C. under reduced pressure. The solution was concentrated, crystallized with ether using a dropping funnel, and stirred to yield a solid. The solid was dried and cefdinir potassium hydrogen sulfate obtained. The yield was 98%, with a content of 98.3% and purity greater than or equal to 99%.

Example 4

To a 100 mL reaction flask, 2.0 g of cefdinir and 20 mL of anhydrous acetone were added and stirred to yield a uniform mixture. 0.496 g of sulfuric acid was diluted with 10 mL of anhydrous acetone, and the resulting solution was dripped slowly into the uniform mixture under an ice bath condition. After the solution was clear, 0.1775 g of potassium methoxide was added and allowed to react for 15 min. Subsequently, acetone was distilled off at 40° C. under reduced pressure. The solution was concentrated, crystallized with ether using a dropping funnel, and stirred to yield a solid. The solid was dried and cefdinir potassium(0.5) hydrogen(1.5) sulfate obtained. The yield was 96.5%, with a content of 97.1% and purity greater than or equal to 99%.

Example 5

To a 100 mL reaction flask, 2.0 g of cefdinir and 20 mL of anhydrous methanol were added and stirred to yield a uniform mixture. 0.496 g of sulfuric acid was diluted with 10 mL of anhydrous methanol, and the resulting solution was dripped slowly into the uniform mixture under an ice bath condition. After the solution was clear, 0.086 g of ammonia gas was inflated and allowed to react under sealing condition for 15 min. Subsequently, methanol was distilled off at 30° C. under reduced pressure. The solution was concentrated, crystallized with hexane using a dropping funnel, and stirred to yield a solid. The solid was dried and cefdinir ammonium hydrogen sulfate obtained. The yield was 96.4%, with a content of 98.6% and purity greater than or equal to 99%.

Example 6

To a 100 mL reaction flask, 2.0 g of cefdinir and 20 mL of anhydrous ethanol were added and stirred to yield a uniform mixture. 0.496 g of sulfuric acid was diluted with 10 mL of anhydrous ethanol, and the resulting solution was dripped slowly into the uniform mixture under an ice bath condition. After the solution was clear, 0.043 g of ammonia gas was inflated and allowed to react under sealing condition for 15 min. Subsequently, ethanol was distilled off at 30° C. under reduced pressure. The solution was concentrated, crystallized with petroleum ether using a dropping funnel, and stirred to yield a solid. The solid was dried and cefdinir ammonium (0.5) hydrogen(1.5) sulfate obtained. The yield was 96.7%, with a content of 97.7% and purity greater than or equal to 99%.

Example 7

To a 100 mL reaction flask, 2.0 g of cefdinir and 20 mL of anhydrous ethanol were added and stirred to yield a uniform mixture. 0.516 g of sodium hydrogen sulfate was mixed with 30 mL of anhydrous ethanol, and the resulting solution was dripped slowly into the uniform mixture. After the solution was clear, ethanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 97%, with a content of 98.4% and purity greater than or equal to 99%.

Example 8

To a 100 mL reaction flask, 2.0 g of cefdinir and 20 mL of anhydrous methanol were added and stirred to yield a uniform mixture. 0.689 g of potassium hydrogen sulfate was mixed with 30 mL of anhydrous methanol, and the resulting solution was dripped slowly into the uniform mixture. After the solution was clear, methanol was distilled off at 35° C. under reduced pressure. The solution was concentrated, crystallized with petroleum ether using a dropping funnel, and stirred to yield a solid. The solid was dried and cefdinir potassium hydrogen sulfate obtained. The yield was 97%, with a content of 98% and purity greater than or equal to 99%.

Example 9

To a 100 mL reaction flask, 2.0 g of cefdinir and 20 mL of anhydrous methanol were added and stirred to yield a uniform mixture. 0.582 g of ammonium hydrogen sulfate was mixed with 30 mL of anhydrous methanol, and the resulting solution was dripped slowly into the uniform mixture. After the solution was clear, methanol was distilled off at 35° C. under reduced pressure. The solution was concentrated, crystallized with ether using a dropping funnel, and stirred to yield a solid. The solid was dried and cefdinir ammonium hydrogen sulfate obtained. The yield was 98%, with a content of 98.7% and purity greater than or equal to 99%.

Example 10

To a 100 mL reaction flask, 2.0 g of cefdinir and 20 mL of anhydrous ethanol were added and stirred to yield a uniform mixture. 0.496 g of phosphoric acid was diluted with 10 mL of anhydrous ethanol, and the resulting solution was dripped slowly into the uniform mixture under an ice bath condition. After the solution was clear, 0.273 g of sodium methoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium dihydrogen phosphate obtained. The yield was 96%, with a content of 98.5% and purity greater than or equal to 99%.

Example 11

To a 100 mL reaction flask, 2.0 g of cefdinir and 20 mL of anhydrous methanol were added and stirred to yield a uniform mixture. 0.4966 g of phosphoric acid was diluted with 10 mL of anhydrous methanol, and the resulting solution was dripped slowly into the uniform mixture under an ice bath condition. After the solution was clear, 0.355 g of potassium methoxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 96.8%, with a content of 98.7% and purity greater than or equal to 99%.

Example 12

To a 100 mL reaction flask, 2.0 g of cefdinir and 20 mL of anhydrous acetone were added and stirred to yield a uniform mixture. 0.4966 g of phosphoric acid was diluted with 10 mL of anhydrous acetone, and the resulting solution was dripped slowly into the uniform mixture under an ice bath condition. After the solution was clear, 0.086 g of ammonia gas was inflated and allowed to react for 25 min under sealing condition. Subsequently, acetone was distilled off at 30° C. under reduced pressure. The solution was concentrated, crystallized with ether using a dropping funnel, and stirred to yield a solid. The solid was dried and cefdinir ammonium dihydrogen phosphate obtained. The yield was 92.4%, with a content of 98.6% and purity greater than or equal to 99%.

Example 13

To a 100 mL reaction flask, 2.0 g of cefdinir and 20 mL of anhydrous methanol were added and stirred to yield a uniform mixture. 0.607 g of sodium dihydrogen phosphate was mixed with 40 mL of anhydrous methanol, and the resulting solution was dripped slowly into the uniform mixture. After the solution was clear, methanol was distilled off at 35° C. under reduced pressure. The solution was concentrated, crystallized with hexane using a dropping funnel, and stirred to yield a solid. The solid was dried and cefdinir sodium dihydrogen phosphate obtained. The yield was 96.8%, with a content of 98.7% and purity greater than or equal to 99%.

Example 14

To a 100 mL reaction flask, 2.0 g of cefdinir and 20 mL of dimethylformamide (DMF) were added and stirred to yield a uniform mixture. 0.607 g of sodium dihydrogen phosphate was mixed with 40 mL of DMF, and the resulting solution was dripped slowly into the uniform mixture. After the solution was clear, DMF was distilled off at 35° C. under reduced pressure. The solution was concentrated, crystallized with hexane using a dropping funnel, and stirred to yield a solid. The solid was dried and cefdinir sodium dihydrogen phosphate obtained. The yield was 96.7%, with a content of 97.5% and purity greater than or equal to 99%.

Example 15

To a 100 mL reaction flask, 2.0 g of cefdinir and 20 mL of anhydrous ethanol were added and stirred to yield a uniform mixture. 0.688 g of potassium dihydrogen phosphate was mixed with 30 mL of anhydrous ethanol, and the resulting solution was dripped slowly into the uniform mixture. After the solution was clear, ethanol was distilled off at 35° C. under reduced pressure. The solution was concentrated, crystallized with petroleum ether using a dropping funnel, and stirred to yield a solid. The solid was dried and cefdinir potassium dihydrogen phosphate obtained. The yield was 93.6%, with a content of 98.7% and purity greater than or equal to 99%.

Example 16

To a 100 mL reaction flask, 2.0 g of cefdinir and 20 mL of dimethylsulfoxide (DMSO) were added and stirred to yield a uniform mixture. 0.688 g of potassium dihydrogen phosphate was mixed with 30 mL of DMSO, and the resulting solution was dripped slowly into the uniform mixture. After the solution was clear, DMSO was distilled off at 35° C. under reduced pressure. The solution was concentrated, crystallized with petroleum ether using a dropping funnel, and stirred to yield a solid. The solid was dried and cefdinir potassium dihydrogen phosphate obtained. The yield was 95.4%, with a content of 97.2% and purity greater than or equal to 99%.

Example 17

To a 100 mL reaction flask, 2.0 g of cefdinir and 20 mL of anhydrous ethanol were added and stirred to yield a uniform mixture. 0.582 g of ammonium dihydrogen phosphate was mixed with 30 mL of anhydrous ethanol, and the resulting solution was dripped slowly into the uniform mixture. After the solution was clear, ethanol was distilled off at 35° C. under reduced pressure. The solution was concentrated, crystallized with ether using a dropping funnel, and stirred to yield a solid. The solid was dried and cefdinir ammonium dihydrogen phosphate obtained. The yield was 96.4%, with a content of 98.7% and purity greater than or equal to 99%.

Example 18

To a 100 mL reaction flask, 5.06 mmol of cefdinir and 20 mL of anhydrous ethanol were added and stirred to yield a uniform mixture. 0.496 g of sulfuric acid was mixed with 10 mL of anhydrous ethanol, and the resulting solution was dripped slowly into the uniform mixture. After the solution was clear, 5.06 mmol of sodium ethoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 98.2%, with a content of 98.3% and purity greater than or equal to 99%.

Example 19

To a 100 mL reaction flask, 5.06 mmol of cefdinir and 20 mL of anhydrous ethanol were added and stirred to yield a uniform mixture. 0.496 g of sulfuric acid was mixed with 10 mL of anhydrous ethanol, and the resulting solution was dripped slowly into the uniform mixture. After the solution was clear, 2.53 mmol of potassium propoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir potassium(0.5) hydrogen(1.5) sulfate obtained. The yield was 98.3%, with a content of 98.8% and purity greater than or equal to 99%.

Example 20

To a 100 mL reaction flask, 5.06 mmol of cefdinir and 20 mL of anhydrous acetone were added and stirred to yield a uniform mixture. 0.496 g of sulfuric acid was mixed with 10 mL of anhydrous acetone, and the resulting solution was dripped slowly into the uniform mixture. After the solution was clear, 5.06 mmol of cesium butoxide was added and allowed to react for 15 min. Subsequently, acetone was distilled off at 40° C. under reduced pressure. The solution was concentrated, crystallized with ether using a dropping funnel, and stirred to yield a solid. The solid was dried and cefdinir cesium hydrogen sulfate obtained. The yield was 97.3%, with a content of 98.5% and purity greater than or equal to 99%.

Example 21

To a 100 mL reaction flask, 5.06 mmol of cefdinir and 20 mL of anhydrous acetone were added and stirred to yield a uniform mixture. 0.496 g of sulfuric acid was mixed with 10 mL of anhydrous acetone, and the resulting solution was dripped slowly into the uniform mixture. After the solution was clear, 2.53 mmol of potassium isopropoxide was added and allowed to react for 15 min. Subsequently, acetone was distilled off at 40° C. under reduced pressure. The solution was concentrated, crystallized with ether using a dropping funnel, and stirred to yield a solid. The solid was dried and cefdinir potassium(0.5) hydrogen(1.5) sulfate obtained. The yield was 96.5%, with a content of 97.1% and purity greater than or equal to 99%.

Example 22

To a 100 mL reaction flask, 5.06 mmol of cefdinir and 20 mL of anhydrous methanol were added and stirred to yield a uniform mixture. 0.496 g of sulfuric acid was mixed with 10 mL of anhydrous methanol, and the resulting solution was dripped slowly into the uniform mixture. After the solution was clear, 2.53 mmol of ammonia water was added and allowed to react for 15 min. Subsequently, methanol was distilled off at 30° C. under reduced pressure. The solution was concentrated, crystallized with hexane using a dropping funnel, and stirred to yield a solid. The solid was dried and cefdinir ammonium hydrogen sulfate obtained. The yield was 96.4%, with a content of 98.6% and purity greater than or equal to 99%.

Example 23

To a 100 mL reaction flask, 5.06 mmol of cefdinir and 20 mL of anhydrous ethanol were added and stirred to yield a uniform mixture. 0.496 g of sulfuric acid was mixed with 10 mL of anhydrous ethanol, and the resulting solution was dripped slowly into the uniform mixture. After the solution was clear, 5.06 mmol of sodium tert-butoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 98.6%, with a content of 97.3% and purity greater than or equal to 99%.

Example 24

To a 100 mL reaction flask, 5.06 mmol of cefdinir and 20 mL of anhydrous ethanol were added and stirred to yield a uniform mixture. 0.496 g of sulfuric acid was mixed with 10 mL of anhydrous ethanol, and the resulting solution was dripped slowly into the uniform mixture. After the solution was clear, 2.53 mmol of potassium acetate was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir potassium(0.5) hydrogen(1.5) sulfate obtained. The yield was 95.3%, with a content of 97.8% and purity greater than or equal to 99%.

Example 25

To a 100 mL reaction flask, 5.06 mmol of cefdinir and 20 mL of anhydrous acetone were added and stirred to yield a uniform mixture. 0.496 g of sulfuric acid was mixed with 10 mL of anhydrous acetone, and the resulting solution was dripped slowly into the uniform mixture. After the solution was clear, 5.06 mmol of cesium propionate was added and allowed to react for 15 min. Subsequently, acetone was distilled off at 40° C. under reduced pressure. The solution was concentrated, crystallized with ether using a dropping funnel, and stirred to yield a solid. The solid was dried and cefdinir cesium hydrogen sulfate obtained. The yield was 96.3%, with a content of 98.4% and purity greater than or equal to 99%.

Example 26

To a 100 mL reaction flask, 5.06 mmol of cefdinir and 20 mL of anhydrous acetone were added and stirred to yield a uniform mixture. 0.496 g of sulfuric acid was mixed with 10 mL of anhydrous acetone, and the resulting solution was dripped slowly into the uniform mixture. After the solution was clear, 2.53 mmol of sodium isopropoxide was added and allowed to react for 15 min. Subsequently, acetone was distilled off at 40° C. under reduced pressure. The solution was concentrated, crystallized with ether using a dropping funnel, and stirred to yield a solid. The solid was dried and cefdinir sodium(0.5) hydrogen(1.5) sulfate obtained. The yield was 96.5%, with a content of 97.1% and purity greater than or equal to 99%.

Example 27

To a 100 mL reaction flask, 5.06 mmol of cefdinir and 20 mL of anhydrous ethanol were added and stirred to yield a uniform mixture. 0.496 g of sulfuric acid was mixed with 10 mL of anhydrous ethanol, and the resulting solution was dripped slowly into the uniform mixture. After the solution was clear, 5.06 mmol of sodium tert-butyrate was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 96.6%, with a content of 96.7% and purity greater than or equal to 99%.

Example 28

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of sodium ethoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium dihydrogen phosphate obtained. The yield was 96.8%, with a content of 97.5% and purity greater than or equal to 99%.

Example 29

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of potassium propoxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen sulfate obtained. The yield was 97.3%, with a content of 96.5% and purity greater than or equal to 99%.

Example 30

To a 100 mL reaction flask, 5.06 mmol of cefdinir and 20 mL of anhydrous acetone were added and stirred to yield a uniform mixture. 0.4966 g of phosphoric acid was mixed with 10 mL of anhydrous acetone, and the resulting solution was dripped slowly into the uniform mixture. After the solution was clear, 5.06 mmol of ammonia water was added and allowed to react for 25 min. Subsequently, acetone was distilled off at 30° C. under reduced pressure. The solution was concentrated, crystallized with ether using a dropping funnel, and stirred to yield a solid. The solid was dried and cefdinir ammonium dihydrogen phosphate obtained. The yield was 95.4%, with a content of 96.6% and purity greater than or equal to 99%.

Example 31

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of cesium butoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir cesium dihydrogen phosphate obtained. The yield was 96.8%, with a content of 97.5% and purity greater than or equal to 99%.

Example 32

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of potassium isopropoxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 97.5%, with a content of 97.3% and purity greater than or equal to 99%.

Example 33

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of sodium tert-butoxide was added and allowed to react for 15 min. Subsequently, ethanol was distilled off at 35° C. under reduced pressure. The solution was concentrated, crystallized with petroleum ether using a dropping funnel, and stirred to yield a solid. The solid was dried and cefdinir sodium dihydrogen phosphate obtained. The yield was 98.1%, with a content of 97.6% and purity greater than or equal to 99%.

Example 34

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of potassium acetate was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 93.6%, with a content of 96.3% and purity greater than or equal to 99%.

Example 35

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of sodium acetate was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir sodium dihydrogen phosphate obtained. The yield was 92.6%, with a content of 97.3% and purity greater than or equal to 99%.

Example 36

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of sodium tert-propionate was added and allowed to react for 15 min. Subsequently, ethanol was distilled off at 35° C. under reduced pressure. The solution was concentrated, crystallized with petroleum ether using a dropping funnel, and stirred to yield a solid. The solid was dried and cefdinir sodium dihydrogen phosphate obtained. The yield was 95.2%, with a content of 98.6% and purity greater than or equal to 99%.

Example 37

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of potassium butyrate was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 92.6%, with a content of 98.3% and purity greater than or equal to 99%.

Example 38

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of cesium butyrate was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 92.6%, with a content of 97.3% and purity greater than or equal to 99%.

Example 39

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of sodium tert-hydroxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium dihydrogen phosphate obtained. The yield was 97.2%, with a content of 96.2% and purity greater than or equal to 99%.

Example 40

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of potassium hydroxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir potassium dihydrogen phosphate obtained. The yield was 90.6%, with a content of 97.7% and purity greater than or equal to 99%.

Example 41

To a 100 mL reaction flask, 5.06 mmol of cefdinir and 20 mL of anhydrous methanol were added and stirred to yield a uniform mixture. 0.4966 g of phosphoric acid was mixed with 10 mL of anhydrous methanol, and the resulting solution was dripped slowly into the uniform mixture. After the solution was clear, 5.06 mmol of cesium hydroxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir cesium dihydrogen phosphate obtained. The yield was 89.6%, with a content of 98.3% and purity greater than or equal to 99%.

Example 42

To a 100 mL reaction flask, 5.06 mmol of cefdinir and 20 mL of anhydrous ethanol were added and stirred to yield a uniform mixture. 5.06 mmol of sulfuric acid was mixed with 10 mL of anhydrous ethanol, and the resulting solution was dripped slowly into the uniform mixture. After the solution was clear, 5.06 mmol of sodium tert-butoxide was added and allowed to react for 15 min. Subsequently, ethanol was distilled off at 35° C. under reduced pressure. The solution was concentrated, crystallized with ether using a dropping funnel, and stirred to yield a solid. The solid was dried and cefdinir sodium hydrogen sulfate obtained. The yield was 96.2%, with a content of 98.5% and purity greater than or equal to 99%.

Example 43

To a 100 mL reaction flask, 5.06 mmol of cefdinir and 20 mL of anhydrous methanol were added and stirred to yield a uniform mixture. 5.06 mmol of sulfuric acid was mixed with 10 mL of anhydrous methanol, and the resulting solution was dripped slowly into the uniform mixture. After the solution was clear, 5.06 mmol of potassium hydroxide was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir sodium hydrogen sulfate obtained. The yield was 90.6%, with a content of 97.7% and purity greater than or equal to 99%.

Example 44

To a 100 mL reaction flask, 5.06 mmol of cefdinir and 20 mL of anhydrous ethanol were added and stirred to yield a uniform mixture. 5.06 mmol of sulfuric acid was mixed with 10 mL of anhydrous ethanol, and the resulting solution was dripped slowly into the uniform mixture. After the solution was clear, 5.06 mmol of cesium hydroxide was added and allowed to react for 15 min. Subsequently, ethanol was distilled off at 40° C. under reduced pressure. The solution was concentrated, crystallized with petroleum ether using a dropping funnel, and stirred to yield a solid. The solid was dried and cefdinir cesium hydrogen sulfate obtained. The yield was 87.6%, with a content of 98.7% and purity greater than or equal to 99%.

Example 45

To a 100 mL reaction flask, 5.06 mmol of cefdinir and 20 mL of anhydrous methanol were added and stirred to yield a uniform mixture. 5.06 mmol of sulfuric acid was mixed with 10 mL of anhydrous methanol, and the resulting solution was dripped slowly into the uniform mixture. After the solution was clear, 5.06 mmol of ammonium acetate was added and allowed to react for 15 min. Subsequently, methanol was distilled off at 40° C. under reduced pressure. The solution was concentrated, crystallized with petroleum ether using a dropping funnel, and stirred to yield a solid. The solid was dried and cefdinir ammonium hydrogen sulfate obtained. The yield was 91.6%, with a content of 98.7% and purity greater than or equal to 99%.

Example 46

To a 100 mL reaction flask, 5.06 mmol of cefdinir and 20 mL of anhydrous ethanol were added and stirred to yield a uniform mixture. 5.06 mmol of sulfuric acid was mixed with 10 mL of anhydrous ethanol, and the resulting solution was dripped slowly into the uniform mixture. After the solution was clear, 5.06 mmol of ammonium propionate was added and allowed to react for 15 min. Subsequently, ethanol was distilled off at 40° C. under reduced pressure. The solution was concentrated, crystallized with petroleum ether using a dropping funnel, and stirred to yield a solid. The solid was dried and cefdinir ammonium hydrogen sulfate obtained. The yield was 89.6%, with a content of 98.1% and purity greater than or equal to 99%.

Example 47

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of ammonium acetate was added and allowed to react for 15 min. Subsequently, methanol was distilled off at 35° C. under reduced pressure. The solution was concentrated, crystallized with ether using a dropping funnel, and stirred to yield a solid. The solid was dried and cefdinir ammonium dihydrogen phosphate obtained. The yield was 94.2%, with a content of 97.6% and purity greater than or equal to 99%.

Example 48

To a 100 mL reaction flask, 5.06 mmol of cefdinir and 20 mL of anhydrous ethanol were added and stirred to yield a uniform mixture. 0.496 g of phosphoric acid was mixed with 10 mL of anhydrous ethanol, and the resulting solution was dripped slowly into the uniform mixture. After the solution was clear, 5.06 mmol of ammonium acetate was added and allowed to react for 15 min. Subsequently, methanol was distilled off at 35° C. under reduced pressure. The solution was concentrated, crystallized with petroleum ether using a dropping funnel, and stirred to yield a solid. The solid was dried and cefdinir ammonium dihydrogen phosphate obtained. The yield was 89.2%, with a content of 98.6% and purity greater than or equal to 99%.

Example 49

INDUSTRIAL APPLICABILITY

Cefdinir is hard soluble hardly soluble in water. The solubility of the compounds of the invention has been increased by 100 times. Table 1 lists the solubility of the compounds of the invention.)

TABLE 1

| No. | Compound | Solubility |
| --- | --- | --- |
| 1 | Cefdinir sodium(0.5) hydrogen(1.5) sulfate | Soluble |
| 2 | Cefdinir potassium(0.5) hydrogen(1.5) sulfate | Soluble |

TABLE 1-continued

| No. | Compound | Solubility |
| --- | --- | --- |
| 3 | Cefdinir ammonium(0.5) hydrogen(1.5) sulfate | Soluble |
| 4 | Cefdinir sodium hydrogen sulfate | Slightly soluble |
| 5 | Cefdinir potassium hydrogen sulfate | Slightly soluble |
| 6 | Cefdinir ammonium hydrogen sulfate | Slightly soluble |
| 7 | Cefdinir sodium dihydrogen phosphate | Slightly soluble |
| 8 | Cefdinir potassium dihydrogen phosphate | Slightly soluble |
| 9 | Cefdinir ammonium dihydrogen phosphate | Slightly soluble |

Beagles, half male and half female, with body weight of 10 kg, were starved for 12 hrs and only water fed. The compounds of the invention were formulated into capsules containing 200 mg of cefdinir and fed to beagles by intragastric administration. The control group was administered with conventional cefdinir capsules. 3 hrs later, the beagles were fed with common food. At 0 h, 0.5 h, 1 h, 1.5 h, 2 h, 2.5 h, 3 h, 4 h, 6 h, 8 h, and 10 h after intragastric administration, 0.5 mL of venous blood was collected respectively to measure the concentration of cefdinir. The results are listed in Table 2.

TABLE 2

Bioavailability comparison between compounds of the invention and conventional cefdinir capsule

| Drugs | Cmax (µg/mL) | Time to peak (h) | AUC(0-10) (µg · h/mL) | Bioavailability percentage increase |
| --- | --- | --- | --- | --- |
| Conventional cefdinir capsule | 21.80 | 3 | 102.11 | / |
| Cefdinir sodium hydrogen sulfate | 65.43 | 3 | 255.27 | 149% |
| Cefdinir sodium(0.5) hydrogen(1.5) sulfate | 50.23 | 3 | 239.96 | 135% |
| Cefdinir potassium hydrogen sulfate | 54.13 | 2.5 | 261.41 | 156% |
| Cefdinir potassium(0.5) hydrogen(1.5) sulfate | 47.65 | 3 | 213.40 | 109% |
| Cefdinir ammonium hydrogen sulfate | 43.63 | 3 | 202.18 | 98% |
| Cefdinir ammonium(0.5) hydrogen(1.5) sulfate | 34.12 | 2.5 | 160.31 | 57% |
| Cefdinir sodium dihydrogen phosphate | 27.28 | 2.5 | 123.55 | 20% |
| Cefdinir potassium dihydrogen phosphate | 30.37 | 3 | 152.15 | 49% |

As shown in Table 2, the bioavailability of the compounds of the invention has been improved by 20% compared with that of conventional cefdinir capsules. The largest increase was 156%.

The production process of cefdinir sodium hydrogen sulfate of Example 1 and cefdinir potassium hydrogen sulfate of Example 3 is stable and thus the bioavailability thereof has improved a lot.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound represented by Formula I

Formula I

[structure of cefdinir] ·$M_mH_nY$, wherein
M represents $Na^+$, $K^+$, $NH_4^+$, or $Cs^+$;
Y represents $SO_4^{2-}$ or $PO_4^{3-}$; and
1) when Y represents $SO_4^{2-}$:
 when m=1, then n=1;
 when m=0.5, then n=1.5; and
2) when Y represents $PO_4^{3-}$: when m=1, then n=2.

2. A method for producing the compound of claim 1, comprising:

contacting cefdinir with an acid and an alkali compound or a compound selected from the group consisting of ammonia, ammonia water, ammonium acetate, ammonium propionate, and ammonium butyrate, wherein said acid is sulfuric acid or phosphoric acid, said alkali compound is sodium methoxide, potassium methoxide, cesium methoxide, sodium ethoxide, potassium ethoxide, cesium ethoxide, sodium propoxide, potassium propoxide, cesium propoxide, sodium butoxide, potassium butoxide, cesium butoxide, sodium isopropoxide, potassium isopropoxide, cesium isopropoxide, sodium tert-butoxide, potassium tert-butoxide, cesium tert-butoxide, sodium acetate, potassium acetate, cesium acetate, sodium propionate, potassium propionate, cesium propionate, sodium butyrate, potassium butyrate, cesium butyrate, sodium hydroxide, potassium hydroxide, or cesium hydroxide; or contacting cefdinir with a hydrogen sulfate salt selected from the group consisting of sodium hydrogen sulfate, potassium hydrogen sulfate, or ammonium hydrogen sulfate, or a dihydrogen phosphate salt selected from the group consisting of sodium dihydrogen phosphate, potassium dihydrogen phosphate, or ammonium dihydrogen phosphate.

3. The compound of claim 1, wherein the compound is:

[structure] ·$NaHSO_4$,

[structure] ·$Na_{1/2}H_{3/2}SO_4$,

[structure] ·$KHSO_4$,

[structure] ·$K_{1/2}H_{3/2}SO_4$,

[structure] ·$NH_4HSO_4$,

[structure] ·$(NH_4)_{1/2}H_{3/2}SO_4$,

[structure] ·$CsHSO_4$, or

[structure] ·$Cs_{1/2}H_{3/2}SO_4$,

4. The compound of claim 1, wherein the compound is:

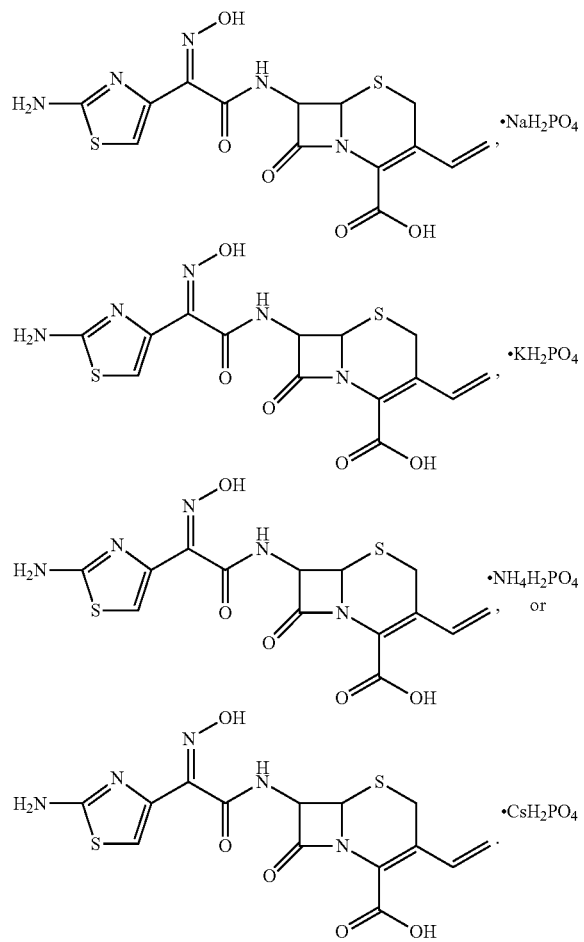

5. A method for preparing the compound of claim 3, the method comprising:
mixing cefdinir and an equimolar amount of sulfuric acid;
adding an alkali compound at a molar ratio of said alkali compound to cefdinir of 0.5:1 or 1:1 to obtain a product, wherein said alkali compound is sodium methoxide, potassium methoxide, cesium methoxide, sodium ethoxide, potassium ethoxide, cesium ethoxide, sodium propoxide, potassium propoxide, cesium propoxide, sodium butoxide, potassium butoxide, cesium butoxide, sodium isopropoxide, potassium isopropoxide, cesium isopropoxide, sodium tert-butoxide, potassium tert-butoxide, cesium tert-butoxide, sodium acetate, potassium acetate, cesium acetate, sodium propionate, potassium propionate, cesium propionate, sodium butyrate, potassium butyrate, cesium butyrate, sodium hydroxide, potassium hydroxide, or cesium hydroxide; and
concentrating, crystallizing with ether, petroleum ether, or hexane, filtering, and drying the product.

6. A method for preparing the compound of claim 3, the method comprising:
mixing cefdinir and an equimolar amount of sulfuric acid;
adding ammonium acetate, ammonia gas, or ammonia water to obtain a product, wherein a molar ratio of ammonium acetate, ammonia gas, or ammonia water to cefdinir is 0.5:1 or 1:1;
concentrating, crystallizing with ether, petroleum ether, or hexane, filtering, and drying the product to yield cefdinir ammonium hydrogen sulfate.

7. A method for preparing the compound of claim 3, the method comprising mixing cefdinir and equimolar amount of sodium hydrogen sulfate, potassium hydrogen sulfate, or ammonium hydrogen sulfate to obtain a product, concentrating, crystallizing with ether, petroleum ether, or hexane, filtering, and drying the product.

8. A method for preparing the compound of claim 4, the method comprising:
mixing cefdinir and an equimolar amount of phosphoric acid,
adding an alkali compound at a molar ratio of said alkali compound to cefdinir of 1:1 to obtain a product, wherein said alkali compound is sodium methoxide, potassium methoxide, cesium methoxide, sodium ethoxide, potassium ethoxide, cesium ethoxide, sodium propoxide, potassium propoxide, cesium propoxide, sodium butoxide, potassium butoxide, cesium butoxide, sodium isopropoxide, potassium isopropoxide, cesium isopropoxide, sodium tert-butoxide, potassium tert-butoxide, cesium tert-butoxide, sodium acetate, potassium acetate, cesium acetate, sodium propionate, potassium propionate, cesium propionate, sodium butyrate, potassium butyrate, cesium butyrate, sodium hydroxide, potassium hydroxide, or cesium hydroxide; and
concentrating, crystallizing with ether, petroleum ether, or hexane, filtering, and drying the product.

9. A method for preparing the compound of claim 4, the method comprising:
mixing cefdinir and equimolar phosphoric acid,
adding ammonium acetate, ammonia gas, or ammonia water at a molar ratio of said ammonium acetate, ammonia gas, or ammonia water to cefdinir of 1:1, and
concentrating, crystallizing with ether, petroleum ether, or hexane, filtering, and drying the product.

10. A method for preparing the compound of claim 4, the method comprising mixing cefdinir and an equimolar amount of sodium dihydrogen phosphate, potassium dihydrogen phosphate, or ammonium dihydrogen phosphate to obtain a product; and concentrating, crystallizing with ether, petroleum ether, or hexane, filtering, and drying the product.

* * * * *